United States Patent
Hodges et al.

(10) Patent No.: US 6,638,415 B1
(45) Date of Patent: Oct. 28, 2003

(54) ANTIOXIDANT SENSOR

(75) Inventors: Alastair Hodges, San Diego, CA (US); Ron Chatelier, San Diego, CA (US)

(73) Assignee: LifeScan, Inc., Milpitas, CA (US)

(*) Notice: Subject to any disclaimer, the term of this patent is extended or adjusted under 35 U.S.C. 154(b) by 61 days.

(21) Appl. No.: 09/615,691

(22) Filed: Jul. 14, 2000

Related U.S. Application Data

(63) Continuation-in-part of application No. 09/314,251, filed on May 18, 1999, now Pat. No. 6,174,420, and a continuation-in-part of application No. PCT/AU99/00152, filed on Mar. 11, 1999, said application No. 09/314,251, is a continuation of application No. 09/068,828, filed as application No. PCT/AU96/00724 on Nov. 15, 1996, now Pat. No. 6,179,979, and a continuation of application No. 08/852,804, filed as application No. PCT/AU96/00723 on Nov. 15, 1996, now Pat. No. 5,942,102.

(30) Foreign Application Priority Data

Nov. 16, 1995 (AU) .............................. PN6619

(51) Int. Cl.$^7$ .............................................. G01N 27/30
(52) U.S. Cl. .................... 205/775; 205/786.5; 205/787; 204/400; 204/403.02; 156/292
(58) Field of Search ................. 204/400, 403, 204/435, 403.01, 403.02; 205/775, 786.5, 787, 792; 156/292

(56) References Cited

U.S. PATENT DOCUMENTS

| | | |
|---|---|---|
| 3,552,928 A | 1/1971 | Fetter |
| 4,053,381 A | 10/1977 | Hamblen et al. |
| 4,076,596 A | 2/1978 | Connery et al. |
| 4,125,372 A | 11/1978 | Kawai et al. |
| 4,168,146 A | 9/1979 | Grubb et al. |

(List continued on next page.)

FOREIGN PATENT DOCUMENTS

| | | |
|---|---|---|
| AU | A-31042/93 | 7/1993 |
| AU | A-54873/94 | 8/1994 |
| DE | 3103464 | 8/1982 |
| DE | 4212280 | 10/1983 |
| DE | 29709141 | 10/1997 |
| EP | 17375 | 10/1980 |
| EP | 127958 | 12/1984 |

(List continued on next page.)

OTHER PUBLICATIONS

Nakamura et al, Biosci. Biotech. Biochem., 57, pp. 379–382, 1993.*
Perfetti et al, J. Assoc. Off. Anal. Chem., 72, pp. 903–906, 1989 (CAS Abstract only).*
Azevedo et al, Anal. Chim. Acta, 387, pp. 175–180, 1999.*
Araujo et al. J. Agric. Food Chem., 46, pp. 168–172, 1998.*
Bard and Faulkner, Electrochemical Methods: Fundamentals and Applications, pp. 22–26, 1980.*
PCT International Search Report for US01/21961.
Abstract for JP 6310746 A; To: Miyahara et al.

(List continued on next page.)

*Primary Examiner*—Nam Nguyen
*Assistant Examiner*—Kaj K. Olsen
(74) *Attorney, Agent, or Firm*—Knobbe Martens Olson & Bear LLP

(57) ABSTRACT

The present invention relates to a device and method for measuring the level of an oxidant or antioxidant analyte in a fluid sample. The device comprises a disposable electrochemical cell, such as a thin layer electrochemical cell, containing a reagent capable of undergoing a redox reaction with the analyte. When the device or method is to be used with slow-reacting analytes, heat may be applied to the sample by a resistive heating element in the device or by an exothermic material contained within the electrochemical cell. Application of heat will accelerate the rate of the redox reaction between the reagent and the analyte and thus facilitate the electrochemical measurement of slow-reacting analytes.

61 Claims, 2 Drawing Sheets

U.S. PATENT DOCUMENTS

| | | |
|---|---|---|
| 4,224,125 A | 9/1980 | Nakamura et al. |
| 4,225,557 A | 9/1980 | Hartl et al. |
| 4,301,412 A | 11/1981 | Hill et al. |
| 4,301,414 A | 11/1981 | Hill et al. |
| 4,319,969 A | 3/1982 | Oda et al. |
| 4,374,013 A | 2/1983 | Enfors |
| 4,404,066 A | 9/1983 | Johnson |
| 4,431,004 A | 2/1984 | Bessman et al. |
| 4,431,507 A | 2/1984 | Nankai et al. |
| 4,508,613 A | 4/1985 | Busta et al. |
| 4,508,821 A | 4/1985 | Mansour et al. |
| 4,517,287 A | 5/1985 | Scheibe et al. |
| 4,517,291 A | 5/1985 | Seago |
| 4,533,440 A | 8/1985 | Kim |
| 4,545,382 A | 10/1985 | Higgins et al. |
| 4,552,840 A | 11/1985 | Riffer |
| 4,604,264 A | 8/1986 | Rothie et al. |
| 4,637,978 A | 1/1987 | Dappen |
| 4,654,197 A | 3/1987 | Lilja et al. |
| 4,711,245 A | 12/1987 | Higgins et al. |
| 4,790,979 A | 12/1988 | Terminiello et al. |
| 4,797,256 A | 1/1989 | Watlington, IV |
| 4,820,489 A | 4/1989 | Rothe et al. |
| 4,871,258 A | 10/1989 | Herpichboehm et al. |
| 4,876,205 A * | 10/1989 | Green et al. ............... 422/98 |
| 4,883,764 A | 11/1989 | Kloepfer |
| 4,897,173 A | 1/1990 | Nankai et al. |
| 4,900,424 A | 2/1990 | Birth et al. |
| 4,919,770 A | 4/1990 | Preidel et al. |
| 4,943,522 A | 7/1990 | Eisinger et al. |
| 4,963,815 A | 10/1990 | Hafeman |
| 4,988,429 A | 1/1991 | Matthiessen |
| 4,994,238 A | 2/1991 | Daffern et al. |
| 5,059,908 A | 10/1991 | Mina |
| 5,096,809 A | 3/1992 | Chen et al. |
| 5,120,420 A | 6/1992 | Nankai et al. |
| 5,122,244 A | 6/1992 | Hoenes et al. |
| 5,126,034 A | 6/1992 | Carter et al. |
| 5,128,015 A | 7/1992 | Szuminsky et al. |
| 5,141,868 A | 8/1992 | Shanks et al. |
| 5,156,972 A | 10/1992 | Issachar |
| 5,179,005 A | 1/1993 | Phillips et al. |
| 5,185,256 A | 2/1993 | Nankai et al. |
| 5,192,415 A | 3/1993 | Yoshioka et al. |
| 5,229,282 A | 7/1993 | Yoshioka et al. |
| 5,239,258 A | 8/1993 | Kauffman |
| 5,272,087 A | 12/1993 | El Murr et al. |
| 5,306,623 A | 4/1994 | Kiser et al. |
| 5,312,590 A | 5/1994 | Gunasingham |
| 5,314,605 A | 5/1994 | Matthiessen |
| 5,320,732 A | 6/1994 | Nankai et al. |
| 5,342,498 A * | 8/1994 | Graves et al. ......... 204/403.06 |
| 5,382,346 A | 1/1995 | Uenoyama et al. |
| 5,384,028 A | 1/1995 | Ito |
| 5,385,846 A | 1/1995 | Kuhn et al. |
| 5,393,399 A | 2/1995 | Van den Berg et al. |
| 5,413,690 A | 5/1995 | Kost et al. |
| 5,418,142 A | 5/1995 | Kiser et al. |
| 5,437,999 A | 8/1995 | Diebold et al. |
| 5,508,171 A | 4/1996 | Walling et al. |
| 5,509,410 A | 4/1996 | Hill et al. |
| 5,518,590 A | 5/1996 | Fang |
| 5,567,302 A | 10/1996 | Song et al. |
| 5,628,890 A | 5/1997 | Carter et al. |
| 5,645,709 A | 7/1997 | Birch et al. |
| 5,776,324 A | 7/1998 | Usala |
| 5,863,400 A | 1/1999 | Drummond et al. |
| 5,942,102 A | 8/1999 | Hodges et al. |
| 5,997,817 A | 12/1999 | Crismore et al. |
| 6,251,260 B1 * | 6/2001 | Heller et al. ............... 204/402 |

FOREIGN PATENT DOCUMENTS

| | | |
|---|---|---|
| EP | 136362 | 4/1985 |
| EP | 171375 | 2/1986 |
| EP | 215446 | 3/1987 |
| EP | 0 251 915 A2 | 1/1988 |
| EP | 0 255 291 A2 | 2/1988 |
| EP | 266204 | 5/1988 |
| EP | 0 278 647 A2 | 8/1988 |
| EP | 289269 | 11/1988 |
| EP | 299779 | 1/1989 |
| EP | 303784 | 2/1989 |
| EP | 0 345 781 A2 | 12/1989 |
| EP | 351891 | 1/1990 |
| EP | 351892 | 1/1990 |
| EP | 359831 | 3/1990 |
| EP | 367432 | 5/1990 |
| EP | 0 400 918 A1 | 12/1990 |
| EP | 401257 | 12/1990 |
| EP | 0 407 800 A2 | 1/1991 |
| EP | 0 415 679 A2 | 3/1991 |
| EP | 418404 | 3/1991 |
| EP | 443231 | 8/1991 |
| EP | 451981 | 10/1991 |
| EP | 0 463 796 A1 | 1/1992 |
| EP | 0 475 692 A1 | 3/1992 |
| EP | 0 479 394 A2 | 4/1992 |
| EP | 0 560 336 A1 | 9/1993 |
| EP | 0 574 134 A2 | 12/1993 |
| EP | 585933 | 3/1994 |
| EP | 593096 | 4/1994 |
| EP | 620437 | 10/1994 |
| EP | 735303 | 3/1995 |
| EP | 658760 | 6/1995 |
| EP | 0 741 186 A2 | 11/1996 |
| EP | 0 764 469 A2 | 3/1997 |
| EP | 0 964 059 A2 | 12/1999 |
| GB | 2020424 | 11/1979 |
| GB | 2154003 | 8/1985 |
| GB | 2154735 | 9/1985 |
| GB | 2186078 | 8/1987 |
| GB | 2 201 248 A | 8/1988 |
| GB | 2204408 | 11/1988 |
| GB | 2215846 | 9/1989 |
| GB | 2235050 | 2/1991 |
| WO | 8904967 | 6/1989 |
| WO | WO 89/08713 | 9/1989 |
| WO | WO 92/15701 | 9/1992 |
| WO | 9402842 | 2/1994 |
| WO | WO 95/16198 | 6/1995 |
| WO | WO 95/21934 | 8/1995 |
| WO | WO 95/28634 | 10/1995 |
| WO | WO 97/00441 | 1/1997 |
| WO | WO 97/18464 | 5/1997 |
| WO | WO 98/11426 | 3/1998 |
| WO | WO 98/43073 | 10/1998 |
| WO | WO 98/43074 | 10/1998 |
| WO | WO 99/46585 | 9/1999 |
| WO | WO 99/53312 | 10/1999 |
| WO | 9958709 | 11/1999 |

OTHER PUBLICATIONS

Anderson, et al., Thin–layer electrochemistry: steady–state methods of studying rate processes, J. Electroanal. Chem., 10(1965) 295–305 No month avaiable.

Bantle., J. P.; Thomas, W.; "Glucose measurement in patients with diabetes mellitus with dermal interstitial fluid"; J. Lab. Clin. Med., vol. 130, No. 4, p. 436, 1997.

He, P. et al.; "Self–assembled biotinylated disulfide derivative monolayer on gold electrode for immobilizing enzymes"; Talanta 44(1997) 855–890.

Hubbard, et al., The Theory and Practice of Electrochemistry with Thin Layer Cells, in Electroanalytical Chemistry, (Bard Ed.), Marcel Deletier, New York, 1970, vol. 4 (pp. 129–214) No month available.

* cited by examiner

ANTIOXIDANT SENSOR

RELATED APPLICATION

This application is continuation-in-part, under 35 U.S.C. §120, of copending International Patent Application No. PCT/AU99/00152, filed on Mar. 11, 1999 under the Patent Cooperation Treaty (PCT), which was published by the International Bureau in English on Sep. 16, 1999, which designates the U.S. and claims the benefit of Australian Provisional Patent Application No. PP 2388, filed Mar. 12, 1998. This application is also a continuation-in-part of Application Ser. No. 09/314,251, filed May 18, 1999, now U.S. Pat. No. 6,174,420. Application Ser. No. 09/314,252 is a continuation of Application Ser. No. 08/852,804, filed May 7, 1997, now U.S. Pat. No. 5,942,102, and a continuation of Application Ser. No. 08/068,828, filed Mar. 15, 1999, now U.S. Pat. No. 6,179,979. Application Ser. No. 08/852,804 is the national phase under 35 U.S.C. §371 of prior PCT International Application No. PCT/AU96/00723 which has an International filing date of Nov. 15, 1996, which designated the United States of America, and which was published by the International Bureau in English on May 22, 1997, and claims the benefit of Australian Provisional Patent Application No. PN 6619, filed Nov. 16, 1995. Application Ser. No. 09/068,828 is the national phase under 35 U.S.C. §371 of prior PCT International Application No. PCT/AU96/00724 which has an International filing date of Nov. 15, 1996, which designated the United States of America, and which was published by the International Bureau in English on May 22, 1997, and claims the benefit of Australian Provisional Patent Application No. PN 6619, filed Nov. 16, 1995.

FIELD OF THE INVENTION

The present invention relates to a device and method for measuring the level of an oxidant or antioxidant analyte in a fluid sample. The device comprises a disposable electrochemical cell containing a reagent capable of directly undergoing a redox reaction with the analyte.

BACKGROUND OF THE INVENTION

An oxidation reaction, broadly defined, involves the transfer of one or more electrons from one molecule or atom (the reducing agent or reductant) to another (the oxidizing agent or oxidant). Oxidation reactions occur in a broad range of systems, e.g., food products, living organisms, and drinking water, and may be detrimental or beneficial. Food products exposed to oxygen may undergo oxidative degradation, resulting in the generation of undesirable flavors and odors, the destruction of fat-soluble vitamins and essential fatty acids, and the production of toxic degradation products. Beneficial oxidation reactions in food products include those between natural or synthetic antioxidants and oxidants, whereby the oxidant is prevented from participating in a detrimental oxidation reaction.

Thus, it is desirable to be able to measure oxidant or antioxidant levels in liquid samples in many fields. For example, it is desirable in terms of manufacturing quality control as well as health monitoring to measure the level of preservatives such as sulfur dioxide in wine or food, the level of ascorbic acid in fruit, vegetables, beverages, and biological fluids, and the level of chlorine or peroxides in water. Most conveniently, these tests are fast and easy to use and be amenable to field as well as laboratory use.

Existing methods for measuring these components require either expensive laboratory apparatus or skilled operators in order for the method to be used successfully. For example, a sensor for detecting antioxidant agents in oil is disclosed in U.S. Pat. No. 5,518,590. However, this sensor is not designed for single, disposable use and does not use a redox agent. It is therefore desirable to have a sensor designed for single, disposable use that can detect oxidant or antioxidant levels in fluid samples through the use of a redox reagent.

SUMMARY OF THE INVENTION

The present invention provides a device and method for measuring oxidant and antioxidant analytes with a disposable sensing element, suitable for a single use, that can be combined with a meter to give a robust, fast, and easy to use test that is amenable to field as well as laboratory use. In particular, the invention relates to the use of an electrochemical sensor that utilizes a redox agent that reacts with the analyte of interest to produce an electrochemically detectable signal.

In one embodiment of the present invention, a device for detecting a presence or an absence of a redox reactive analyte in an aqueous sample is provided, the device including an electrochemical cell having a sensing chamber, a first electrode, a second electrode, an aperture for admitting the sample into the sensing chamber, and a reagent contained within the sensing chamber, wherein the electrochemical cell is designed to be disposed of after use in a single experiment, and wherein the reagent is capable of undergoing a redox reaction directly with the analyte to generate an electrical signal indicative of the presence or absence of the analyte.

In one aspect of this embodiment, the first electrode is a sensing electrode that may consist of platinum, palladium, carbon, indium oxide, tin oxide, gold, iridium, copper, steel, or mixtures thereof. The first electrode may also be silver. The first electrode may be formed by a technique such as sputtering, vapor coating, screen printing, thermal evaporation, ink jet printing, ultrasonic spraying, slot coating, gravure printing and lithography.

In another aspect of this embodiment, the second electrode is a counter electrode. The second electrode may include a metal in contact with a metal salt, for example, silver in contact with silver chloride, silver in contact with silver bromide, silver in contact with silver iodide, mercury in contact with mercurous chloride, or mercury in contact with mercurous sulfate. The second electrode may also be a reference electrode.

In another aspect of this embodiment, the electrochemical cell further includes a third electrode, such as a reference electrode. The third electrode may include a metal in contact with a metal salt, such as silver in contact with silver chloride, silver in contact with silver bromide, silver in contact with silver iodide, mercury in contact with mercurous chloride, and mercury in contact with mercurous sulfate.

In another aspect of this embodiment, the reagent is capable of oxidizing an analyte including an antioxidant. The reagent may include ferricyanide salts, dichromate salts, permanganate salts, vanadium oxides, dichlorophenolindophenol, osmium bipyridine complexes, and quinones.

In another aspect of this embodiment, the reagent is capable of reducing an analyte including an oxidant. The reagent may include iodine, triiodide salts, ferrocyanide salts, ferrocene, $Cu(NH_3)_4^{2+}$ salts, and $Co(NH_3)_6^{3+}$ salts.

In another aspect of this embodiment, the sensing chamber further includes a buffer contained within the sensing chamber. The buffer is selected from the group consisting of phosphates, carbonates, alkali metal salts of mellitic acid, and alkali metal salts of citric acid.

In another aspect of this embodiment, the device further includes a heating element. The heating element may include an electrically resistive heating element or an exothermic substance contained within the sensing chamber, such as aluminum chloride, lithium chloride, lithium bromide, lithium iodide, lithium sulfate, magnesium chloride, magnesium bromide, magnesium iodide, magnesium sulfate, and mixtures thereof.

In another aspect of this embodiment, the sensing chamber includes a support contained within the sensing chamber. Supports may include mesh, nonwoven sheet, fibrous filler, macroporous membrane, sintered powder, and combinations thereof. One or both of the reagent and buffer may be contained within or supported on the support.

In another aspect of this embodiment, the second electrode is mounted in opposing relationship a distance of less than about 500 microns from the first electrode, less than about 150 microns from the first electrode, or less than about 150 microns and greater than about 50 microns from the first electrode.

In another aspect of this embodiment, the device further includes an interface for communication with a meter. The interface may communicate a voltage or a current.

In another aspect of this embodiment, the electrochemical cell includes a thin layer electrochemical cell.

In a second embodiment of the present invention, a method for detecting a presence or an absence of a redox reactive analyte in an aqueous sample is provided which includes providing a device for detecting the presence or absence of an analyte in an aqueous sample, the device including an electrochemical cell having a sensing chamber, a first electrode, a second electrode, an aperture for admitting the sample into the sensing chamber, and a reagent contained within the sensing chamber, wherein the electrochemical cell is designed to be disposed of after use in a single experiment, and wherein the reagent is capable of undergoing a redox reaction directly with the analyte to generate an electrical signal indicative of the presence or absence of the analyte; providing an aqueous sample; allowing the sample to flow through the aperture and into the sensing chamber, such that the sensing chamber is substantially filled; and obtaining an electrochemical measurement indicative of the presence or absence of analyte present in the sample.

In one aspect of this embodiment, the electrochemical measurement is an amperometric measurement, a potentiometric measurement, a coulometric measurement, or a quantitative measurement.

In another aspect of this embodiment, the method includes the further step of heating the sample, wherein the heating step precedes the step of obtaining the electrochemical measurement. Alternatively, the method may include the additional steps of heating the sample, wherein the heating step follows the step of obtaining an electrochemical measurement; and thereafter obtaining a second electrochemical measurement indicative of the presence or absence of a second analyte present in the sample.

In another aspect of this embodiment, the sensing chamber further includes a buffer, for example, phosphate buffer, carbonate buffer, alkali metal salt of mellitic acid, and alkali metal salt of citric acid.

In a third aspect of the present invention, a method for measuring sulfur dioxide in a sample of wine is provided, the sulfur dioxide having a free form and a bound form and being capable of undergoing a redox reaction with a reagent, the redox reaction having a reaction kinetics, wherein the method includes the steps of providing a device, the device including an electrochemical cell having a sensing chamber, a first electrode, a second electrode, an aperture for admitting the sample into the sensing chamber, and a reagent capable of undergoing a redox reaction with sulfur dioxide, wherein the electrochemical cell is designed to be disposed of after use in a single experiment; placing the sample of wine in the electrochemical cell, thereby initiating the redox reaction; and obtaining a first electrochemical measurement indicative of the level of sulfur dioxide in free form.

In one aspect of this embodiment, the method further includes the steps of heating the sample of wine for a period of time sufficient for sulfur dioxide in bound form to react with the reagent, wherein the heating step is conducted after the step of obtaining a first electrochemical measurement; and thereafter obtaining a second electrochemical measurement indicative of the level sulfur dioxide in free form and in bound form combined. Alternatively, the method may include the further steps of obtaining a second electrochemical measurement indicative of the kinetics of reaction of the sulfur dioxide in bound form with the reagent, wherein the second electrochemical measurement is obtained after the step of obtaining a first electrochemical measurement; and calculating the level of bound sulfur dioxide using the kinetics of reaction.

In a fourth aspect of the present invention, a method of manufacture of a device for detecting the presence or absence of a redox reactive analyte in an aqueous sample is provided, the device including an electrochemical cell having a sensing chamber, a first electrode, a second electrode, an aperture for admitting the sample into the sensing chamber, and a reagent contained within the sensing chamber, wherein the electrochemical cell is designed to be disposed of after use in a single experiment, and wherein the reagent is capable of undergoing a redox reaction directly with the analyte to generate an electrical signal indicative of the presence or absence of the analyte, the method including forming an aperture extending through a sheet of electrically resistive material, the aperture defining a side wall of the sensing chamber; mounting a first layer having a first electrode to a first side of the sheet and extending over the aperture, defining a first sensing chamber end wall, the first electrode facing the first side of the sheet; mounting a second layer having a second electrode to a second side of the sheet and extending over the aperture defining a second sensing chamber end wall in substantial overlying registration with the first layer, the second electrode facing the second side of the sheet, whereby the sheet and layers form a strip; forming an aperture in the strip to permit entry of a sample into the sensing chamber; and providing a reagent capable of undergoing a redox reaction directly with the analyte, wherein the reagent is contained within the sensing chamber.

In one aspect of this embodiment, the method includes the further step of providing a vent in the strip to permit escape of air displaced from the sensing chamber when sample fills the sensing chamber. Another further step includes mounting an electrically resistive heating element to the strip.

In a further aspect of this embodiment, the aperture is of a rectangular cross-section.

In a further aspect of this embodiment, at least one of the electrodes includes a noble metal, for example, palladium, platinum, and silver. At least one of the electrodes may be a sputter coated metal deposit. The electrodes may be adhered to the sheet, for example, by an adhesive such as a heat activated adhesive, pressure sensitive adhesive, heat cured adhesive, chemically cured adhesive, hot melt adhesive, or hot flow adhesive.

In a further aspect of this embodiment, the method includes further steps such as providing an exothermic substance or buffer contained within the sensing chamber; printing the reagent or buffer onto at least one wall of the sensing chamber; or providing a support such as mesh, fibrous filler, macroporous membrane, sintered powder, and combinations thereof contained within the sensing chamber. The reagent may be supported on or contained within the support.

In a further aspect of this embodiment, at least the sheet or one of the layers of the device manufactured according to the method is a polymeric material selected from the group consisting of polyester, polystyrene, polycarbonate, polyolefin, and mixtures thereof. Alternatively, at least the sheet or one of the layers is polyethylene terephthalate.

In a further aspect of this embodiment, the second electrode is mounted in opposing relationship a distance of less than about 500 microns from the first electrode; less than about 150 microns from the first electrode; or less than about 150 microns and greater than about 50 microns from the first electrode.

DETAILED DESCRIPTION OF THE PREFERRED EMBODIMENTS

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

The Sample and Analyte

In preferred embodiments, a method and device for measuring oxidant or antioxidant levels in fluid samples is provided. The method and device are applicable to any oxidant or antioxidant that exists in a usefully representative concentration in a fluid sample. Antioxidants that may be analyzed include, for example, sulfur dioxide and ascorbic acid. Oxidants that may be analyzed include, for example, chlorine, bromine iodine, peroxides, hypochlorite, and ozone. Water insoluble oxidants or antioxidants may also be analyzed if an aqueous form can be prepared, e.g., by using a detergent to prepare an emulsion of the water insoluble redox reactive analyte.

Methods and devices for obtaining electrochemical measurements of fluid samples are discussed further in copending U.S. patent application Ser. No. 09/616,433, filed on Jul. 14, 2000, pending entitled "IMMUNOSENSOR," copending U.S. patent application Ser. No. 09/616,512, filed on Jul. 14, 2000, pending entitled "HEMOGLOBIN SENSOR," and copending U.S. patent application Ser. No. 09/616,556, filed on Jul. 14, 2000, now U.S. Pat. No. 6,445,115, entitled "ELECTROCHEMICAL METHOD FOR MEASURING CHEMICAL REACTION RATES," each of which is incorporated herein by reference in its entirety.

The device and method may be used with any analyte-containing sample which is fluid and which is capable of solubilizing the redox reagent to a sufficient extent. Typical samples include beverages such as fruit and vegetable juice, carbonated beverages, drinking water, beer, wine, and spirits. However, it is not intended that the method be limited to comestible samples. If the sample is not in fluid form or is not capable of solubilizing the redox reagent to a sufficient extent, the analyte contained within the sample may be extracted into a suitable fluid using extraction techniques well-known in the art. The sample may be pre-treated prior to its introduction into the electrochemical cell. For example, pH may be adjusted to a desired level by means of a buffer or neutralizing agent, or a substance that renders interfering oxidants or antioxidants nonreactive may be added. The sample may also be preheated before introduction into the cell so as to accelerate the rate at which the redox reaction takes place.

The Electrochemical Cell

Figure 1:
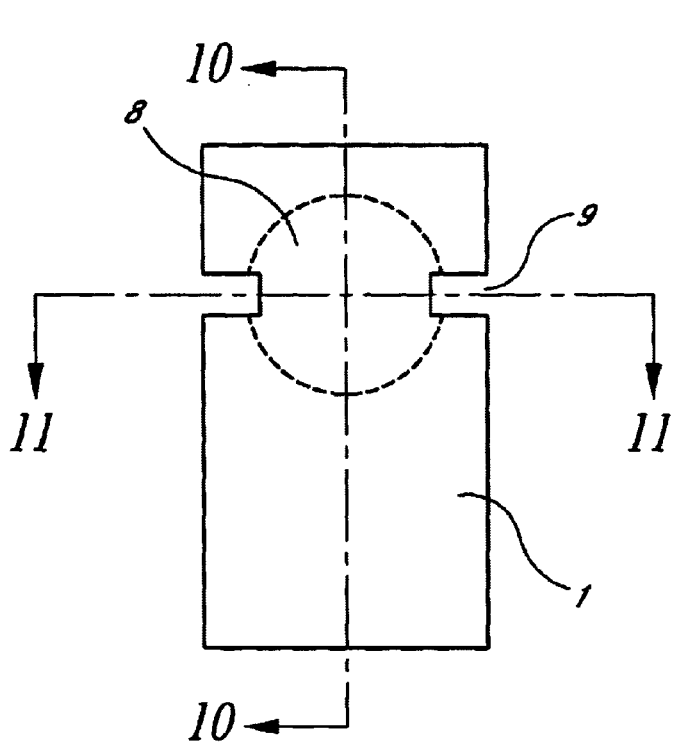
FIG. 1 shows a plan view of an electrochemical cell.
Figure 2:
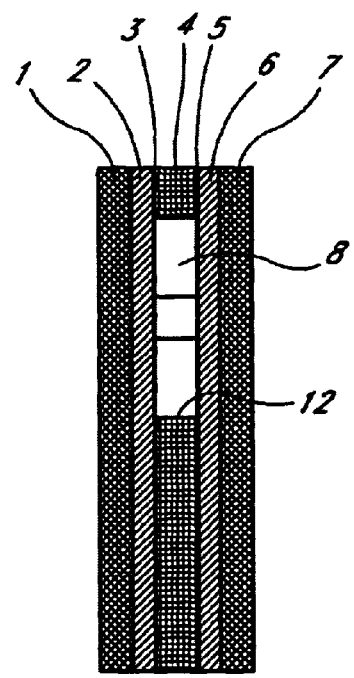
FIG. 2 shows a cross-section view on line 10—10 of FIG. 1.
Figure 3:
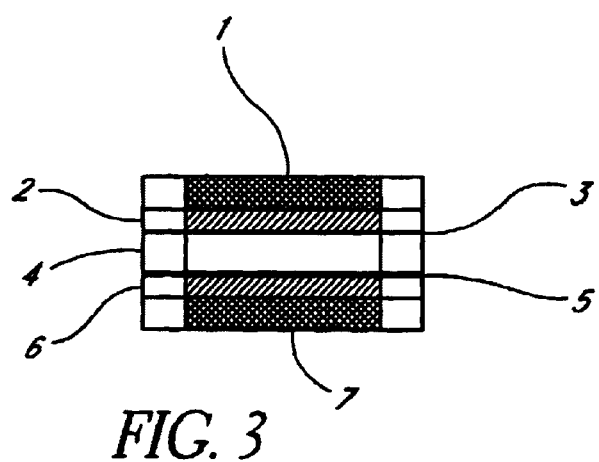
FIG. 3 shows an end-section view on line 11—11 of FIG. 1.

The electrochemical cell of present invention is disposable and designed for use in a single experiment. In a preferred embodiment, the electrochemical cell is a thin layer sensor such as that disclosed in U.S. Pat. No. 5,942,102 (incorporated herein by reference in its entirety). As herein used, the term "thin layer electrochemical cell" refers to a cell having closely spaced electrodes such that reaction products from the counter electrode arrive at the working electrode. In practice, the separation of electrodes in such a cell for measuring glucose in blood will be less than 500 microns, and preferably less than 200 microns. A preferred embodiment of such an electrochemical cell is illustrated in FIGS. 1, 2, and 3. The cell illustrated in FIGS. 1, 2, and 3 includes a polyester core 4 having a circular aperture 8. Aperture 8 defines a cylindrical cell side wall 12. Adhered to one side of core 4 is a polyester sheet 1 having a sputter coating of palladium 2. The sheet is adhered by means of an adhesive 3 to core 4 with palladium 2 adjacent core 4 and covering aperture 8. A second polyester sheet 7 having a second sputter coating of palladium 6 is adhered by means of contact adhesive 5 to the other side of core 4 and covering aperture 8. There is thereby defined a cell having cylindrical side wall 12 closed on each end by palladium metal 2, 6. The assembly is notched at 9 to provide for a solution to be admitted to the cell or to be drawn in by wicking or capillary action and to allow air to escape. The metal films 2, 6 are connected with suitable electrical connections or formations whereby potentials may be applied and currently measured.

Such a thin layer electrochemical cell is prepared by first forming an aperture extending through a sheet of electrically resistive material, the aperture defining a side wall of the electrochemical cell. Suitable electrically resistive materials, which may be used in the sheet containing the aperture, or in other layers in the cell, include, for example, materials such as polyesters, polystyrenes, polycarbonates, polyolefins, polyethylene terephthalate, mixtures thereof, and the like. In a preferred embodiment, the aperture in the sheet is rectangular, however other shapes, e.g., circular, may be used as well.

After the aperture is formed, a first thin electrode layer is then mounted on one side of the sheet of electrically resistive material, extending over the aperture and forming an end wall. The layer may be adhered to the sheet, for example, by means of an adhesive. Suitable adhesives include, for example, heat activated adhesives, pressure sensitive adhesives, heat cured adhesives, chemically cured adhesives, hot melt adhesives, hot flow adhesives, and the like. The electrode layer is prepared by coating (e.g., by sputter coating) a sheet of electrically resistive material with a suitable metal, for example, palladium.

A second thin electrode layer is then mounted on the opposite side of the electrically resistive material, also extending over the aperture, so as to form a second end wall. In a preferred embodiment, the electrode layers are mounted in opposing relationship at a distance of less than about 1 millimeter, desirably less than about 800 microns, more desirably less that about 600, or preferably less than about 500 microns, more preferably less than about 300 to 150 microns, more preferably less than 150 microns, and most preferably between 25, 40, 50, 100 and 150 microns. A second aperture or ingress is then provided for liquid to enter the cell. Such an ingress can be provided by forming a notch along one edge of the device which extends through the electrode layers and aperture. The electrode layers are provided with connection means allowing the sensors to be placed in a measuring circuit.

Chemicals for use in the cell, such as redox reagents, buffers, and other substances, may be supported on the cell electrodes or walls, on one or more independent supports contained within cell, or may be self supporting. If the chemicals are to be supported on the cell electrodes or walls, the chemicals may be applied by use of application techniques well known in the art, such as ink jet printing, screen printing, lithography, ultrasonic spraying, slot coating, gravure printing, and the like. Suitable independent supports may include, but are not limited to, meshes, nonwoven sheets, fibrous fillers, macroporous membranes, and sintered powders. The chemicals for use in the cell may be supported on or contained within a support.

In a preferred embodiment, the materials used within the cell as well as the materials used to construct the cell are in a form amenable to mass production, and the cells themselves are designed to be able to be used for a single experiment then disposed of.

According to the present invention a disposable cell is one that is inexpensive enough to produce that it is economically acceptable to be used only for a single test. Secondly, that the cell may conveniently only be used for a single test. Inconveniently in this context means that steps such as washing and/or reloading of reagents would need to be taken to process the cell after a single use to render it suitable for a subsequent use.

Economically acceptable in this context means that the perceived value of the result of the test to the user is the same or greater than the cost of the cell to purchase and use, the cell purchase price being set by the cost of supplying the cell to the user plus an appropriate mark up. For many applications, this requires that the cells have relatively low materials costs and simple fabrication processes. For example, the electrode materials of the cells should be inexpensive, such as carbon, or be used in sufficiently small amounts such that expensive materials may be used. Screen printing carbon or silver ink is a process suitable for forming electrodes with relatively inexpensive materials. However, if it is desired to use electrode materials such as platinum, palladium, gold or iridium, methods with better material utilization, such as sputtering or evaporative vapor coating, are more suitable as they may give extremely thin films. The substrate materials for the disposable cells also need to be inexpensive. Examples of such inexpensive materials are polymers such as polyvinylchloride, polyimide, polyester and coated papers and cardboard.

Cell assembly methods also need to be amenable to mass production. These methods include fabricating multiple cells on cards and separating the card into individual strips subsequent to the main assembly steps, and web fabrication where the cells are produced on a continuous web, which is subsequently separated into individual strips. Card processes are most suitable when close spatial registration of multiple features is required for the fabrication and/or when stiff cell substrate materials are to be used. Web processes are most suitable when the down web registration of features is not as critical and flexible webs may be used.

The convenient single use requirement for the disposable cell is desirable so that users are not tempted to try to reuse the cell and possibly obtain an inaccurate test result. The single use requirement for the cell may be stated in user instructions accompanying the cell. More preferably, the cell may also be fabricated such that using the cell more than once is difficult or not possible. This may be accomplished, for example, by including reagents that are washed away or consumed during the first test and so are not functional in a second test. Alternatively, the signal of the test may be examined for indications that reagents in the cell have already reacted, such as an abnormally high initial signal, and the test aborted. Another method includes providing a means for breaking electrical connections in the cell after the first test in a cell has been completed.

Cells for measuring antioxidants in the prior art do not satisfy these requirements for disposability. The cell disclosed by Richard J. Price et al. in Analyst, November 1991, Vol. 116, pages 1121–1123 uses a silver wire, a platinum wire and a platinum disc as the electrodes for a cell measuring antioxidants in oil. Platinum wires are too expensive to be used in a single use device in this application, and the cell is designed for continuous monitoring, not a single test. In U.S. Pat. No. 5,518,590, Fang discloses another cell for measuring antioxidants in oil. This cell also uses platinum wire as an electrode and is also designed for continuous use, namely, effectively conducting multiple tests over time. This cell also requires a liquid or gel layer containing a polar solvent. Such a device is not conducive to mass fabrication and storage due to the need to contain the liquid components, possibly over long periods, prior to use.

The Electrodes

At least one of the electrodes in the cell is a sensing electrode, defined as an electrode sensitive to the amount of reduced redox agent in the antioxidant case or oxidized redox agent in the oxidant case. In the case of a potentiometric sensor wherein the potential of the sensing electrode is indicative of the level of analyte present, a second electrode acting as reference electrode is present which acts to provide a reference potential.

In the case of an amperometric sensor wherein the sensing electrode current is indicative of the level of analyte in the sample, at least one other electrode is present which functions as a counter electrode to complete the electrical circuit. This second electrode may also function as a reference electrode. Alternatively, a separate electrode may perform the function of a reference electrode.

Materials suitable for the sensing, counter, and reference electrodes must be compatible with the redox reagents present in the device. Compatible materials will not react chemically with the redox reagent or any other substance present in the cell. Examples of such suitable materials include, but are not limited to, platinum, palladium, carbon, indium oxide, tin oxide, mixed indium/tin oxides, gold, silver, iridium and mixtures thereof. These materials may be formed into electrode structures by any suitable method, for example, by sputtering, vapor coating, screen printing, thermal evaporation or lithography. In preferred embodiments, the material is sputtered or screen printed to form the electrode structures.

Non-limiting examples of materials suitable for use in the reference electrode include metal/metal salt systems such as silver in contact with silver chloride, silver bromide or silver iodide, and mercury in contact mercurous chloride or mercurous sulfate. The metal may be deposited by any suitable method and then brought into contact with the appropriate metal salt. Suitable methods include, for example, electrolysis in a suitable salt solution or chemical oxidation. Such metal/metal salt systems provide better potential control in potentiometric measurement methods than do single metal component systems. In a preferred embodiment, the metal/metal salt electrode systems are used as a separate reference electrode in an amperometric sensor.

The Redox Reagent

Suitable redox reagents include those which are capable of undergoing a redox reaction with the analyte of interest. Examples of redox reagents suitable for use in analyzing antioxidant analytes include, but are not limited to, salts of ferricyanide, dichromate, osmium bipyridine complexes, vanadium oxides, and permanganate. Organic redox reagents such as dichlorophenolindophenol, and quinones are also suitable. In a preferred embodiment, the redox reagent for analyzing an antioxidant is ferricyanide. Examples of reagents suitable for use in analyzing oxidant analytes include iodine and salts of triiodide, ferrocyanide, ferrocene, $Cu(NH_3)_4^{2+}$, and $Co(NH_3)_6^{3+}$. In a preferred embodiment, the redox reagent for measuring an oxidant is ferrocyanide.

The Buffer

Optionally, a buffer may be present along with the redox reagent in dried form in the electrochemical cell. If a buffer is used, it is present in an amount such that the resulting pH level is suitable for adjusting the oxidizing (or reducing) potential of the redox reagent to a level suitable for oxidizing (or reducing) the analytes of interest but not other species that it is not desired to detect. The buffer is present in a sufficient amount so as to substantially maintain the pH of the sample at the desired level during the test. Examples of buffers suitable for use include phosphates, carbonates, alkali metal salts of mellitic acid, and alkali metal, salts of citric acid. The choice of buffer will depend on the desired pH. The buffer is selected so as not to react with the redox reagent. Alkali buffers are preferred for use in conjunction with carbonated beverages.

Other Substances Present Within The Cell

In addition to redox reagents and buffers, other substances may also be present within the cell. Such substances include, for example, viscosity enhancers and low molecular weight polymers. Hydrophilic substances may also be contained within the cell, such as polyethylene glycol, polyacrylic acid, dextran, and surfactants such as those marketed by Rohm & Haas Company of Philadelphia, Pa., under the trade name Triton™ or by ICI Americas Inc. of Wilmington, Del., under the trade name Tween™. Such substances may enhance the fill rate of the cell, provide a more stable measurement, and inhibit evaporation in small volume samples.

Method for Measuring Analyte Concentration

In measuring an antioxidant or oxidant analyte present in a sample, the sample is introduced into the sensor cell, whereupon the sample dissolves the dried reagents present in the cell. The redox reagent then reacts with any antioxidants or oxidants of interest present in the sample to form the reduced or oxidized form of the redox reagent. In the case of a potentiometric sensor, the resulting ratio of oxidized to reduced form of the redox reagent fixes the potential of the sensing electrode relative to the reference electrode. This potential is then used as a measure of the concentration of the analyte originally in the sample.

In a preferred embodiment, the sensing cell is operated as an amperometric sensor. According to this embodiment, the reduced (or oxidized) redox reagent formed by reaction with the analytes of choice is electrochemically oxidized (or reduced) at the sensing electrode. The current resulting from this electrochemical reaction is then used to measure the concentration of analytes originally in the sample. In other embodiments, the sensor is operated in potentiometric or coulometric mode.

The cell's electrodes are used to produce an electrical signal, i.e., a voltage or current, readable by an attached meter. In a preferred embodiment, an interface for connecting the cell to the meter is provided. The meter may display the measurement in a visual, audio or other form, or may store the measurement in electronic form.

Heating the Sample

Certain oxidant or antioxidant analytes are slow to react with the redox reagent. To accelerate the reaction, and thus reduce the time required to obtain the measurement, the sample may be heated. In a preferred embodiment, a means for heating the sample is provided in the disposable electrochemical sensor device.

Two suitable means of heating the cell are described in WO99/46585 (incorporated herein by reference in its entirety). WO99/46585 discloses a method for determining the concentration of an analyte in a sample wherein the sample is heated and the concentration of the analyte (or species representative of the analyte) is measured at a predetermined point on a reaction profile (defined as the relationship of one reaction variable to another) by temperature independent means. The sample may be heated either by an exothermic reaction produced upon contact of the sample with a suitable reagent or reagents or the sample may be heated electrically by means of a current applied to resistive elements associated with the cell.

One method of heating the sample via exothermic reaction involves placing in the electrochemical cell a reagent that liberates heat on contact with the sample. Examples of such reagents include salts which give out heat when they dissolve, such as aluminum chloride, lithium halide salts, lithium sulfate, magnesium halide salts and magnesium sulfate. The reagent or reagents used to liberate heat must not adversely affect the function of the other active elements in the cell, such as by corroding electrode materials, reacting with the analyte so as to affect its response, or adversely interacting with other reagents present.

Figure 4:
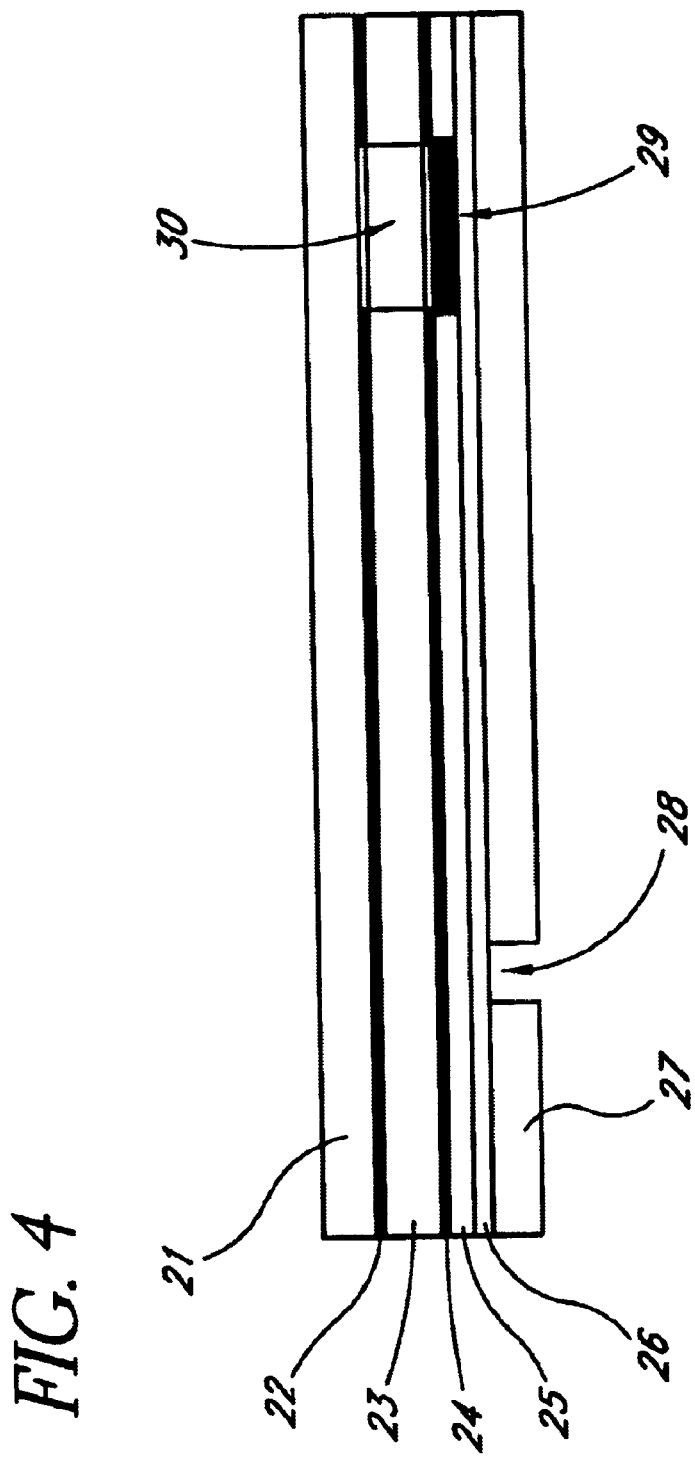
FIG. 4 shows schematically a heated electrochemical cell in a cross section taken longitudinally through the midline of the cell.

When the sample is to be heated electrically, the electrochemical cell may be equipped with an electrically resistive element. FIG. 4 shows a preferred embodiment of an electrochemical sensor as described in WO99/46585. The sensor comprises a nonconducting substrate 21, bearing a first electrode 22, a separator layer 23 having a circular aperture 30 punched out which defines a circular cell wall 30. The first electrode 22 defines one end of the cell, the other end being defined by the second electrode layer 24, which is carried by a second nonconducting layer 25. A metal foil layer 26, provides electrical contact to a resistive bridge 29 formed in the second nonconducting layer 25. An insulating layer 27 provides insulation against heat loss through the metal foil layer 26. An aperture 28 is formed in insulating layer 27 to allow access for electrical connection to foil 26.

In preferred embodiments, resistive elements may be prepared by impregnating one or more of the nonconducting layers carrying an electrode layer with a substance such as carbon particles. The nonconducting layers may include such materials as plastic or rubber. The impregnated rubber or plastic layer forms a resistive bridge between the electrode of the electrochemical cell and the metal foil layer. When a potential is applied across the resistive element, heat is generated in the impregnated rubber or plastic layer, which in turn heats the sample in the electrochemical cell. Alternatively, at least two low resistance tracks joined by a high resistance track can be formed on an external face of the sensor. In such an embodiment, the low resistance tracks serve to make contact with the meter and the high resistance track forms the electrically resistive element.

Multiple Cell Devices

In certain situations, it may be desirable to measure more than one oxidant and/or antioxidant analyte in a sample. This may be accomplished by using an array of two or more electrochemical cells as described above. Each cell contains a redox reagent suited for use with one of the analytes present in the sample. Each cell is also equipped with buffers or heating means, if required for that particular analyte. Such an array of cells may be used not only to determine the concentration of known analytes of interest, but may also be used to screen a sample of unknown analyte composition for the presence or absence of a variety of analytes.

Various embodiments of a cell array are contemplated. In one embodiment, cell construction techniques as described above are used to fabricate a device having multiple sensing chambers and electrodes but sharing one or more layers of insulating material. In another embodiment, two or more electrochemical cells as described above are adhered together, either directly to each other or to a separate support material. Alternatively, two or more cells as described above, but containing different reagents, may be packaged together in a kit suitable for use in a particular application, i.e., a analysis of a sample containing multiple analytes or different forms of the same analyte.

Analysis of Sulfur Dioxide in Wine

One example of an analysis wherein it is useful to heat the sample is the measurement of sulfur dioxide in wine. Sulfur dioxide in wine functions as an antioxidant and is typically present in two forms: the free form and the bound form. The free form is more quickly oxidized by the redox reagent in the sensor than is the bound form. It is normally desirable to measure both the free and bound forms of sulfur dioxide in wine. To measure both forms, a heating means is included in the electrochemical cell. A sample of the wine is placed in the sensing cavity, whereupon the redox reagent present reacts quickly with the free sulfur dioxide to produce a sensor signal. This signal is analyzed and then heat is applied to the sample via the heating means. In a preferred embodiment, heating is applied with a slow rise in temperature so as to avoid excessive evaporation of the sample. After a suitable period of time at elevated temperature, the bound sulfur dioxide reacts with the redox reagent, thereby producing a second sensor signal. From these two signals the free concentration and total concentration of sulfur dioxide in the sample are obtained, and thus, by difference, are the free and bound form concentrations obtained. While this two-step method is beneficial for obtaining the concentration of the free and bound forms of sulfur dioxide in wine, the invention also contemplates other uses for such a method. For example, a two (or more) step method may be used for analyzing suitable samples containing an analyte having two or more forms with different reaction kinetics, or samples containing two or more different analytes each having different reaction kinetics.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. A device for detecting a presence or an absence of a redox reactive analyte in an aqueous sample, the device comprising an electrochemical cell having a sensing chamber, a first electrode, a second electrode wherein the second electrode is mounted in opposing relationship a distance of less than about 500 microns from the first electrode, an aperture for admitting the sample into the sensing chamber, and a reagent contained within the sensing chamber, wherein the electrochemical cell contains a quantity of the reagent sufficient for only a single experiment, and wherein the reagent is capable of undergoing a redox reaction directly with the analyte to generate an electrical signal indicative of the presence or absence of the analyte, the device further comprising a heating element, wherein the heating element is an exothermic substance contained within the sensing chamber.

2. The device of claim 1, wherein the first electrode comprises a sensing electrode.

3. The device of claim 1, wherein the first electrode comprises a material selected from the group consisting of platinum, palladium, carbon, indium oxide, tin oxide, gold, iridium, copper, steel, and mixtures thereof.

4. The device of claim 1, wherein the first electrode comprises silver.

5. The device of claim 1, wherein the first electrode is formed by a technique selected from the group consisting of sputtering, vapor coating, screen printing, thermal evaporation, ink jet printing, ultrasonic spraying, slot coating, gravure printing and lithography.

6. The device of claim 1, wherein the second electrode comprises a counter electrode.

7. The device of claim 6, the electrochemical cell further comprising a third electrode.

8. The device of claim 7, wherein the third electrode comprises a reference electrode.

9. The device of claim 8, wherein the third electrode comprises a metal in contact with a metal salt.

10. The device of claim 9, wherein the metal in contact with the metal salt is selected from the group consisting of silver in contact with silver chloride, silver in contact with silver bromide, silver in contact with silver iodide, mercury in contact with mercurous chloride, and mercury in contact with mercurous sulfate.

11. The device of claim 1, wherein the second electrode comprises a metal in contact with a metal salt.

12. The device of claim 11, wherein the metal in contact with a metal salt is selected from the group consisting of silver in contact with silver chloride, silver in contact with silver bromide, silver in contact with silver iodide, mercury in contact with mercurous chloride, and mercury in contact with mercurous sulfate.

13. The device of claim 1, wherein the second electrode comprises a reference electrode.

14. The device of claim 1, wherein the reagent is capable of oxidizing an analyte comprising an antioxidant.

15. The device of claim 14, wherein the reagent is selected from the group consisting of ferricyanide salts, dichromate salts, permanganate salts, vanadium oxides, dichlorophenolindophenol, osmium bipyridine complexes, and quinones.

16. The device of claim 1, wherein the reagent is capable of reducing an analyte comprising an oxidant.

17. The device of claim 16, wherein the reagent is selected from the group consisting of iodine, triiodide salts, ferrocyanide salts, ferrocene, $Cu(NH_3)_4^{2+}$ salts, and $Co(NH_3)_6^{3+}$ salts.

18. The device of claim 1, the sensing chamber further comprising a buffer, wherein the buffer is contained within the sensing chamber.

19. The device of claim 18, wherein the buffer is selected from the group consisting of phosphates, carbonates, alkali metal salts of mellitic acid, and alkali metal salts of citric acid.

20. The device of claim 1, further comprising an additional heating element, the additional heating element comprising an electrically resistive heating element.

21. The device of claim 1, wherein the exothermic substance is selected from the group consisting of aluminum chloride, lithium chloride, lithium bromide, lithium iodide, lithium sulfate, magnesium chloride, magnesium bromide, magnesium iodide, magnesium sulfate, and mixtures thereof.

22. The device of claim 1, the sensing chamber further comprising a support, the support contained within the sensing chamber.

23. The device of claim 22, wherein the support is a material selected from the group consisting of mesh, non-woven sheet, fibrous filler, macroporous membrane, sintered powder, and combinations thereof.

24. The device of claim 22, wherein the reagent is contained within or supported on the support.

25. The device of claim 22, wherein the buffer is contained within or supported on the support.

26. The device of claim 1, wherein the second electrode is mounted in opposing relationship a distance of less than about 150 microns from the first electrode.

27. The device according to claim 1, wherein the second electrode is mounted in opposing relationship a distance of less than about 150 microns and greater than about 50 microns from the first electrode.

28. The device of claim 1, further comprising an interface for communication with a meter.

29. The device of claim 28, wherein the interface communicates a voltage or a current.

30. The device of claim 1, wherein the electrochemical cell comprises a thin layer electrochemical cell.

31. A method for detecting a presence or an absence of a redox reactive analyte in an aqueous sample, the method comprising:
  providing a device for detecting the presence or absence of an analyte in an aqueous sample, the device comprising an electrochemical cell having a sensing chamber, a first electrode, a second electrode wherein the second electrode is mounted in opposing relationship a distance of less than about 500 microns from the first electrode, an aperture for admitting the sample into the sensing chamber, and a reagent contained within the sensing chamber, wherein the electrochemical cell contains a quantity of the reagent sufficient for only a single experiment, and wherein the reagent is capable of undergoing a redox reaction directly with the analyte to generate an electrical signal indicative of the presence or absence of the analyte;
  providing an aqueous sample;
  allowing the sample to flow through the aperture and into the sensing chamber, such that the sensing chamber is substantially filled; and
  obtaining an electrochemical measurement indicative of the presence or absence of analyte present in the sample;
  heating the sample, wherein the heating step follows the step of obtaining an electrochemical measurement; and thereafter
  obtaining a second electrochemical measurement indicative of the presence or absence of a second analyte present in the sample.

32. The method of claim 31, wherein the electrochemical measurement is an amperometric measurement.

33. The method of claim 31, wherein the electrochemical measurement is a potentiometric measurement.

34. The method of claim 31, wherein the electrochemical measurement is a coulometric measurement.

35. The method of claim 31, wherein the electrochemical measurement is a quantitative measurement.

36. The method of claim 31, further comprising an additional step of heating the sample, wherein the additional heating step precedes the step of obtaining the electrochemical measurement.

37. The method of claim 31, the sensing chamber further comprising a buffer.

38. The method of claim 37, wherein the buffer is selected from the group consisting of phosphate buffer, carbonate buffer, alkali metal salt of mellitic acid, and alkali metal salt of citric acid.

39. A method for measuring sulfur dioxide in a sample of wine, the sulfur dioxide having a free form and a bound form and being capable of undergoing a redox reaction with a reagent, the redox reaction having a reaction kinetics, wherein the method comprises:
  providing a device, the device comprising an electrochemical cell having a sensing chamber, a first electrode, a second electrode wherein the second electrode is mounted in opposing relationship a distance of less than about 500 microns from the first electrode, an aperture for admitting the sample into the sensing chamber, and a reagent capable of undergoing a redox reaction with sulfur dioxide, wherein the electrochemical cell contains a quantity of the reagent sufficient for only a single experiment;
  placing the sample of wine in the electrochemical cell, thereby initiating the redox reaction; and obtaining a first electrochemical measurement indicative of the level of sulfur dioxide in free form.

40. The method according to claim 39, further comprising the steps of:
   heating the sample of wine for a period of time sufficient for sulfur dioxide in bound form to react with the reagent, wherein the heating step is conducted after the step of obtaining a first electrochemical measurement; and thereafter
   obtaining a second electrochemical measurement indicative of the level sulfur dioxide in free form and in bound form combined.

41. The method according to claim 39, further comprising the steps of:
   obtaining a second electrochemical measurement indicative of the kinetics of reaction of the sulfur dioxide in bound form with the reagent, wherein the second, electrochemical measurement is obtained after the step of obtaining a first electrochemical measurement; and
   calculating the level of bound sulfur dioxide using the kinetics of reaction.

42. A method of manufacture of a device for detecting the presence or absence of a redox reactive analyte in an aqueous sample, the device comprising an electrochemical cell having a sensing chamber, a first electrode, a second electrode wherein the second electrode is mounted in opposing relationship a distance of less than about 500 microns from the first electrode, an aperture for admitting the sample into the sensing chamber, and a reagent contained within the sensing chamber, wherein the electrochemical cell contains a quantity of the reagent sufficient for only a single experiment, and wherein the reagent is capable of undergoing a redox reaction directly with the analyte to generate an electrical signal indicative of the presence or absence of the analyte, the method comprising:
   forming an aperture extending through a sheet of electrically resistive material, the aperture defining a side wall of the sensing chamber;
   mounting a first layer having a first electrode to a first side of the sheet and extending over the aperture, defining a first sensing chamber end wall, the first electrode facing the first side of the sheet;
   mounting a second layer having a second electrode to a second side of the sheet and extending over the aperture defining a second sensing chamber end wall in substantial overlying registration with the first layer, the second electrode facing the second side of the sheet, whereby the sheet and layers form a strip;
   forming an aperture in the strip to permit entry of a sample into the sensing chamber;
   providing a reagent capable of undergoing a redox reaction directly with the analyte, wherein the reagent is contained within the sensing chamber; and
   providing an exothermic substance, the exothermic substance being contained within the sensing chamber.

43. The method according to claim 42, further comprising the step of providing a vent in the strip to permit escape of air displaced from the sensing chamber when sample fills the sensing chamber.

44. The method according to claim 42, further comprising the step of mounting an electrically resistive heating element to the strip.

45. The method according to claim 42, wherein at least one of the electrodes comprises a noble metal.

46. The method according to claim 42, wherein the noble metal is selected from the group consisting of palladium, platinum, and silver.

47. The method according to claim 42, wherein the aperture is of a rectangular cross-section.

48. The method according to claim 42, wherein at least one of the electrodes is a sputter coated metal deposit.

49. The method according to claim 42, wherein the electrodes are adhered to the sheet.

50. The method according to claim 49, wherein the electrodes are adhered to the sheet by an adhesive.

51. The method according to claim 50, wherein the adhesive is selected from the group consisting of heat activated adhesive, pressure sensitive adhesive, heat cured adhesive, chemically cured adhesive, hot melt adhesive, and hot flow adhesive.

52. The method according to claim 42, further comprising the step of providing a buffer, the buffer being contained within the sensing chamber.

53. The method according to claim 52, further comprising the step of printing the buffer onto at least one wall of the sensing chamber.

54. The method according to claim 42, further comprising the step of printing the reagent onto at least one wall of the sensing chamber.

55. The method according to claim 42, further comprising the step of providing a support, the support contained within the sensing chamber.

56. The method according to claim 55, wherein the support is selected from the group consisting of mesh, fibrous filler, macroporous membrane, sintered powder, and combinations thereof.

57. The method according to claim 55, wherein the reagent is supported on or contained within the support.

58. The method according to claim 42, wherein at least the sheet or one of the layers comprises a polymeric material selected from the group consisting of polyester, polystyrene, polycarbonate, polyolefin, and mixtures thereof.

59. The method according to claim 42, wherein at least the sheet or one of the layers comprises polyethylene terephthalate.

60. The method according to claim 42, wherein the second electrode is mounted in opposing relationship a distance of less than about 150 microns from the first electrode.

61. The method according to claim 42, wherein the second electrode is mounted in opposing relationship a distance of less than about 150 microns and greater than about 50 microns from the first electrode.

* * * * *